United States Patent [19]

Heilmann et al.

[11] Patent Number: 5,468,847
[45] Date of Patent: Nov. 21, 1995

[54] METHOD OF ISOLATING AND PURIFYING A BIOMACROMOLECULE

[75] Inventors: Steven M. Heilmann, Afton; Gary J. Drtina, Woodbury; Philip D. Eitzman, Lake Elmo; Louis C. Haddad, Mendota Heights; Frederick W. Hyde, New Brighton; Todd W. Johnson, Minneapolis; Jerald K. Rassmussen, Stillwater; Michael G. Williams, Vadnais Heights, all of Minn.

[73] Assignee: Minnesota Mining and Manufacturing Company, St. Paul, Minn.

[21] Appl. No.: 209,700

[22] Filed: Mar. 10, 1994

[51] Int. Cl.$^6$ ............... C07K 1/16; C07K 1/18; B01D 15/08; B01D 61/08
[52] U.S. Cl. ............ 530/413; 530/415; 530/416; 530/417; 210/500.23; 210/634; 210/637; 210/638; 210/645; 210/650; 210/656; 210/660
[58] Field of Search ............... 530/413, 414, 530/415, 416, 417, 427; 536/127; 436/71; 554/29, 70, 83, 100, 175, 191; 210/634, 500.27, 638, 654, 635, 655, 637, 656, 645, 660, 650, 651, 672, 653, 676, 679, 677, 683, 685, 500.23, 500.29, 500.42

[56] References Cited

U.S. PATENT DOCUMENTS

| 3,058,594 | 6/1960 | Hultgren | 210/493.5 |
| 4,150,563 | 4/1979 | Minarik et al. | 73/61.56 |

(List continued on next page.)

FOREIGN PATENT DOCUMENTS

| 1179283 | 12/1984 | Canada . |
| 3406562 | 8/1985 | Germany . |
| 1486305 | 9/1977 | United Kingdom . |
| 2230278 | 10/1990 | United Kingdom . |
| WOA9207879 | 5/1992 | WIPO . |

OTHER PUBLICATIONS

Sigma Catalog 1993 Hydrophobic Resins pp. 1629–1633.
Pierce 1989 Handbook and General Catalog, 1989, Pierce, p. 62, No. 20055.
Supelco Chromatography Products Catalog, 1994, Supelco, pp. 300 and 304; feature "P" (mesh support).
Patent Abstracts of Japan (vol. 14, No. 566) (C–0789), abstract of JP,A,02 245 190 Dec. 17, 1990.
Patent Abstracts of Japan (vol. 10, No. 230) (C–365), abstract of JP,A,61 067 474 Sep. 8, 1986.
J. R. Ford, et al., *Biotechnol. & Bioeng. Symp.* No. 3, 1972, 267–284.
T. J. Harrington, et al., *Enzyme Microb. Technol.*, 1992, 14, 813–818.
Schmidt-Kastner, et al., *Biochem. Eng. [Intl. Congr.]*, 1986 (publ. 1987), 111–131.
A. M. Wilhelm and J. P. Riba, *J. Chromatog.*, 1989, 484, 211–223.

*Primary Examiner*—Michael G. Wityshyn
*Assistant Examiner*—Nancy J. Degen
*Attorney, Agent, or Firm*—Gary L. Griswold; Walter N. Kirn; Lorraine R. Sherman

[57] ABSTRACT

The invention provides a method of separating a biomacromolecule which comprises the steps of providing a separation system including a filter element which comprises a composite filtration medium, the composite filtration medium comprising a filtration layer on the upstream surface of which are located insoluble stationary phase particulates, the particulates being capable of binding to a biomacromolecule or class of biomacromolecules, a reservoir containing a solution mixture comprising at least one biomacromolecule as solute, and a pump and associated tubing to form a closed loop assembly, and recirculation pumping the solution mixture through the filter cartridge so as to bind the at least one biomacromolecule to the stationary phase particulate so as to form a biomacromolecule:stationary phase particulate product. An eluting solution can be pumped through the closed loop assembly which is capable of reversing the biomacromolecule:stationary phase particulate product binding interaction so as to liberate the biomacromolecule.

30 Claims, 3 Drawing Sheets

U.S. PATENT DOCUMENTS

| | | | |
|---|---|---|---|
| 4,208,309 | 6/1980 | Kraemer et al. | 521/53 |
| 4,238,334 | 12/1980 | Halbjoster | 210/679 |
| 4,242,461 | 12/1980 | Bartoli et al. | 435/288 |
| 4,331,541 | 5/1982 | Akiyama et al. | 210/679 |
| 4,384,957 | 5/1983 | Crowder, III et al. | 210/656 |
| 4,404,285 | 9/1983 | Hou | 436/16 |
| 4,488,969 | 12/1984 | Hou | 210/679 |
| 4,663,163 | 5/1987 | Hou et al. | 210/645 |
| 4,774,004 | 9/1988 | Gruenewaelder | 210/663 |
| 4,839,419 | 6/1989 | Kraemer et al. | 525/54.1 |
| 4,842,739 | 6/1989 | Tang | 210/489 |
| 4,857,461 | 8/1989 | Egerer et al. | 435/94 |
| 4,963,494 | 10/1990 | Hibino et al. | 435/288 |
| 4,966,707 | 10/1990 | Cussler et al. | 210/632 |
| 5,028,335 | 7/1991 | Sleytr et al. | 210/638 |
| 5,047,154 | 9/1991 | Comstock et al. | 210/636 |
| 5,051,184 | 9/1991 | Taylor | 210/632 |
| 5,155,144 | 10/1992 | Manganaro et al. | 523/134 |
| 5,310,688 | 5/1994 | Zale et al. | 436/535 |

METHOD OF ISOLATING AND PURIFYING A BIOMACROMOLECULE

FIELD OF THE INVENTION

This invention relates to a method for the separation and purification of a biomacromolecule from a solution which comprises one or a plurality of biomacromolecules, especially on a large scale. The purified biomacromolecules are useful therapeutic or diagnostic agents.

BACKGROUND OF THE INVENTION

Biomacromolecules are constituents or products of living cells and include proteins, carbohydrates, lipids, and nucleic acids. Detection and quantification as well as isolation and purification of these materials have long been objectives of investigators. Detection and quantification are important diagnostically, for example, as indicators of various physiological conditions such as diseases. Isolation and purification of biomacromolecules are important for therapeutic purposes such as when administered to patients having a deficiency in the particular biomacromolecule, when utilized as a biocompatible carrier of some medicament, and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

Chromatography is a separation and purification operation that is often performed on biological product mixtures. It is a technique based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the de-binding effects of a mobile phase compared to solutes which interact less strongly and, in this fashion, separation and purification can be effected.

Efforts to utilize polydisperse particles as stationary phases for separating biomacromolecules by incorporation within a porous fiber matrix are disclosed in U.S. Pat. Nos. 4,384,957 and 4,488,969. Resultant composite sheet structures were cut into circular shapes and stacked to form columns.

Liquid cartridge filters have been developed over the years which represent a highly efficient format for the interaction of a liquid stream and a solid matrix. Furthermore, these filters operate at relatively high flow rates, e.g., liters per minute, and at relatively low pressures.

In tangential flow or radial membrane cartridge filters, the filtering element is presented in a plane parallel to the liquid stream flow, and two effluents or permeates are produced, one filtered or processed by passing through the filtering element and another not. While these filter arrangements operate at low pressures and the unprocessed permeate can in theory be recycled, these systems are intrinsically more complicated and slower to completely process a liquid stream because of relatively low flow through the element; also, if filtering elements were modified in some fashion to retain biomacromolecules, complete retention would be required in one pass through the element.

In "dead end" filters the filtering element is presented perpendicularly to the direction of flow of the liquid stream. All the liquid stream is required to pass through the element and only one permeate is produced. Considered as a separation unit in which separation is occurring by interaction with a stationary phase on or within the filtering element, the dead end cartridge filter would be analogous to a very wide, but shallow column. At high flow rates single pass retention of the biomacromolecule may be relatively low but by repeatedly cycling the effluent high percentages of the biomacromolecule can be retained.

Bioseparations have been conducted using modified filter cartridges. U.S. Patent No. 5,155,144 discloses microporous sheets comprising modified polysaccharide particulates such as diethylaminoethyl cellulose, a typical ion exchange chromatography stationary phase, dispersed within a polymeric medium. It is suggested that these sheets can further be configured into a dead end filter cartridge. Employing recirculation of effluent, a lead ion treated resin was evaluated as a generally shallow column between two stainless steel grids for the analytical separation of D-xylose (cf. A. M. Wilhelm and J. P. Riba, J. Chromatog., 1989, 484, 211–223). The resulting packed bed reactor system was evaluated to determine hydrodynamic conditions for particles for ultimate employment in columns for production liquid chromatography at relatively high system pressures and low flow rates.

U.S. Pat. No. 4,774,004 discloses the use of cartridge filters that are generally "charged" with filtration aids which are layered silicates that essentially function as ion exchange media and, optionally, kieselguhr or activated carbon. The resultant structures were useful for removing surfactants and "dissolved soil" from dry cleaning solvents. Details of the charging procedure, quantities of filtration aids employed, recycle flow rates, and operating system pressures are scant. No separation of one or more biomacromolecules was conducted nor contemplated.

SUMMARY OF THE INVENTION

Briefly, this invention provides a method of separating (can include purifying) a biomacromolecule comprising the steps of (a) providing a separation system containing a dead end filter cartridge comprising a composite filter medium on the upstream surface of which are located stationary phase particulates capable of binding with a biomacromolecule, a reservoir containing a solution comprising at least one biomacromolecule as solute, and a pump and associated tubing to form a closed loop assembly, (b) recirculation pumping the solution through the filter cartridge so as to selectively bind one biomacromolecule or more than one biomacromolecule in the case of related biomacromolecules to the stationary phase particulate so as to form a biomacromolecule:stationary phase particulate product, and (c) optionally, pumping an eluting solution through the closed loop assembly which is capable of reversing the biomacromolecule:stationary phase particulate product binding interaction so as to liberate the biomacromolecule.

For use in this method, this invention provides a filter element comprising a composite filtration medium, the composite filtration medium comprising a filtration layer on the upstream surface of which are located insoluble stationary phase particulates, the particulates being capable of binding to a biomacromolecule.

In another aspect, there is provided a filter cartridge including the above-described filter element.

In yet another aspect, there is provided a separation filter assembly comprising the filter cartridge and a filter cartridge housing, the stationary phase particulate of the composite filtration medium of the invention being capable of binding a biomacromolecule.

This invention provides a method for separating, purifying, or concentrating a biomacromolecule solute from a solution containing other biomacromolecular solute compounds. The method is conducted at relatively low pressure and is especially suitable for large scale bioseparations.

More particularly, the method of the invention provides a liquid filter cartridge comprising a composite filter medium contained within a suitable housing which is connected to a pump and a solution reservoir. The novel composite filter medium is prepared by a process in which a slurry comprising at least one of chromatographic adsorption, ion exchange, affinity, and hydrophobic stationary phase particulates in a liquid (generally water) is pumped through to partially load a filtration layer such that the stationary phase particulates are principally located on the upstream surface of the filtration layer. A solution of a biological mixture to be separated is then pumped through the filter cartridge in order for the biological solute of interest to be separated from the solution by a binding association with the stationary phase. The resultant solution with the selected biomacromolecular solute removed (or its concentration decreased) may be utilized. The procedure is more commonly performed, however, to recover the separated biological solute. During elution or an isolation step, a solution which can effect reversal of the binding to the stationary phase is next pumped through the filter cartridge, preferably in a volume of solution smaller than the initial volume of the biological solution mixture. Binding of the selected biomacromolecule solute from a solution which passes through the filter element can be by sorption or chemical reaction. Preferred binding mechanisms include adsorption, ion exchange, hydrophobic association, and affinity binding. In a separate step, the binding can be reversed so as to isolate and purify the previously bound biomacromolecule.

In this application:

"biomacromolecule" means a component or product of a cell such as a protein, carbohydrate, lipid, or nucleic acid, possessing a molecular weight of at least 500;

"filtration layer" means a sheet-like woven or nonwoven porous material which can comprise one or more individual layers which can be combined to provide a single sheet; the average pore size is greater than 1 micrometer and up to 50 micrometers;

"composite filtration medium" means a filtration layer comprising a layer of stationary phase particulates located on the upstream surface thereof; the medium can sustain a flux rate of at least 0.01 cm/min at a filter cartridge pressure of at most 0.25 MegaPascals (MPa);

"filter element" or "filtering element" or "filtration element" means a composite filtration medium configured for fluid passage; it is the actual component of a separation filter assembly which accomplishes the filtering/separating/purifying operation;

"filter cartridge" means a dead end filtering device which is preferably cylindrical in shape;

"filter cartridge housing" means a support structure for a filter cartridge;

"separation filter assembly" means a housing containing a dead end filter cartridge comprising a composite filter medium on the upstream surface of which are located stationary phase particulates;

"separation system" means a solution mixture comprising at least one biomacromolecular solute contained in a reservoir, a separation filter assembly, a pump, and associated tubing;

"flux rate" means the velocity of a liquid stream passing through a filtering element and is equal to flow rate divided by the surface area of the filtration layer. Described in this way, flow of a liquid stream can be characterized and is independent of the size of the filtration layer. Flux rate also contributes to pressure drop across a filter, i.e., increased flux rates generally mean increased system pressures. In commercial filter cartridge applications, it is highly desirable to provide a filter of minimum size which will process a maximum amount of liquid stream. Therefore, it is desirable that flux rate be increased by increasing the flow rate;

"stationary phase particulates" mean insoluble particulates that can form a binding association with a biomacromolecular component of interest in a solution mixture. Specific binding associations include: adsorption, ion exchange, hydrophobic, and affinity interactions;

"cryo-poor" means blood plasma from which undissolved solids have been removed after a freeze/thaw cycle;

"insoluble" means not more than 1 part particulates dissolves in 100 parts of solvent at 23° C.; and "filter cartridge pressure" means the difference between inlet, or upstream, and outlet, or downstream, pressures across the filter cartridge unit in a separation system.

The present invention process overcomes problems of prior art cartridge filters employed for the separation of biomacromolecules. Prior art filters containing stationary phase particulates within a filtering element present manufacturing challenges and offer only limited capacities. The hazards of air-borne particulates are well known and related manufacturing problems can easily arise in construction of filter cartridges which comprise small stationary phase particulates entrapped within a filter element. Prior art systems are also capacity limited in that more particulates must be loaded into a filtering element in order to increase the quantity of biomacromolecule separated. Higher loading of particulates gives rise to a filtering element with reduced porosity and concomitant increased operating system pressures.

The present invention overcomes these problems of prior art filters by significantly reducing handling of dry stationary phase particulates and by providing high loading capacity of particulates at relatively low filter cartridge pressures.

DETAILED DESCRIPTION OF THE DRAWING

Figure 1:
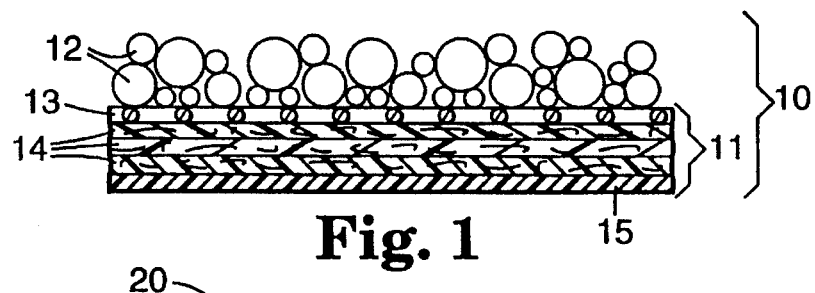
FIG. 1 is a schematic illustration of a cross-section of a composite filtration medium comprising a filtration layer which comprises a layer of stationary phase particulates located on the upstream surface thereof.

FIG. 1 is a schematic illustration of a cross-section of a composite filtration medium 10 comprising a preferred nonwoven web as surface filtration layer 11 which can be one or more individual layers, upon the upstream surface of which are located insoluble stationary phase particulates 12. The nonwoven filtration layer 11 which possesses uniform porosity and well-defined pores can comprise coarse upstream prefilter layer 13, filtration layers 14 comprising a multiplicity of nonwoven filtration layers having increasingly finer downstream porosity, and a downstream nonwoven cover layer 15.

Figure 2:
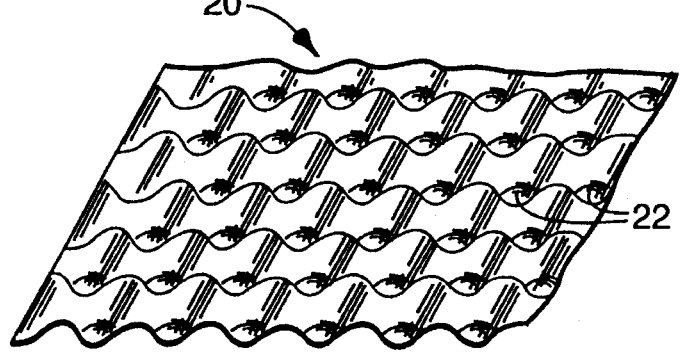
FIG. 2 is a perspective view of the embossed pattern on a composite filtration medium of the invention.

FIG. 2 is an illustration of a preferred embodiment of the invention. There is shown a perspective view of a nonpleated portion of a pattern of embossed shapes 22 on composite filtration medium 20 utilized to produce filter cartridges. Embossing is conducted to increase frontal surface area and more completely define the surface filtering element. The insoluble stationary phase particulates are omitted from the illustration for clarity.

Figure 3:
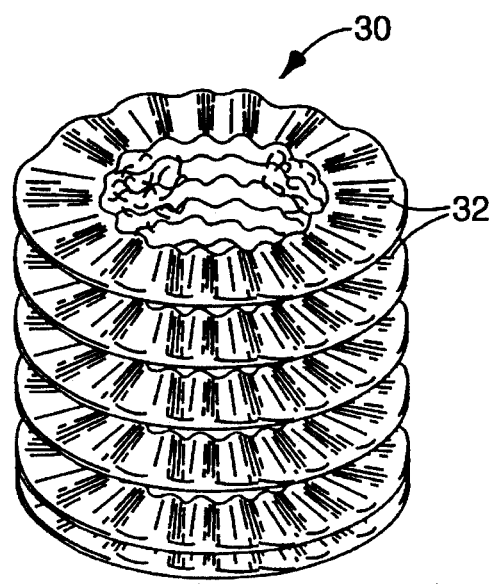
FIG. 3 is a perspective view of a cylindrically pleated filter element of the invention.

FIG. 3 is a perspective view of a longitudinally extended cylindrically pleated filter element 30 of a preferred embodiment of the invention; radial pleats 32 of preferred compound radially pleated filtration element 30 of the invention are shown; again, stationary phase particulates are omitted for clarity.

Figure 4:
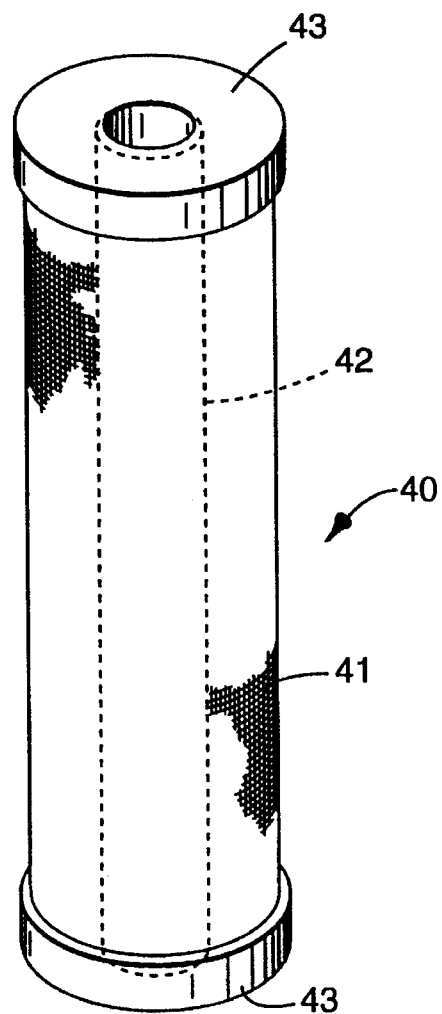
FIG. 4 is a perspective view of support members for a cylindrical filter cartridge of the invention.

FIG. 4 is a perspective view which illustrates inner and outer supplemental support members for cylindrical filter cartridge 40, which is a preferred embodiment of the invention. External support structure 41, such as a scrim or screen with a multiplicity of holes, can provide additional support in an inward-out fluid flow mode to reduce the likelihood of rupturing the filter element. Similarly, inner support structure 42 consisting of a scrim or screen, or a porous casing or similar construction can provide support to prevent the filter element (not shown) from collapsing under high pressure applications in a preferred outward-in fluid flow situation. In both cases, the supplemental support structures are normally attached to endpieces 43 of the filter cartridge to provide an integral unit.

Figure 5:
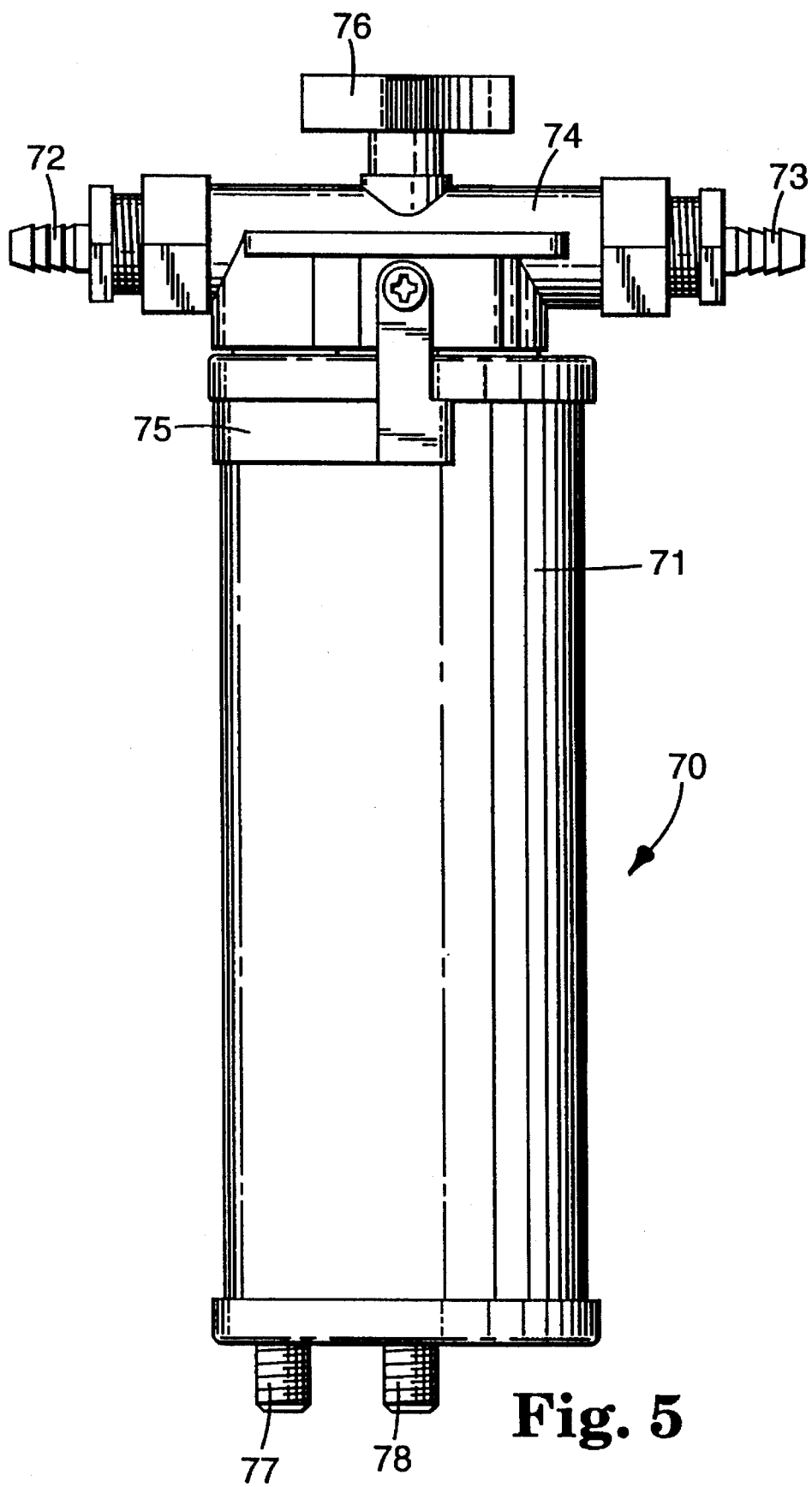
FIG. 5 is a perspective view of a separation filter assembly of the invention.

FIG. 5 is a perspective view of a separation filter assembly 70 of the invention, this being a preferred embodiment of the invention. Filter housing 71 contains a filter cartridge (not shown). In the separation loop, inlet port 72 allows the solution mixture to enter the filter cartridge in the preferred outward-in mode. The liquid exits separation filter assembly 70 through outlet port 73. In a preferred assembly, the separation head 74 is attached to filter housing 71 by a mechanical clamp 75 employing a threaded bolt (not shown) with tension adjusting control knob 76. In the isolation loop, inlet port 77 allows de-binding solution to enter the filter cartridge in the preferred outward-in mode, and the resultant solution now containing the desired biomacromolecule solute exits separation filter assembly 70 through outlet port 78.

Figure 6:
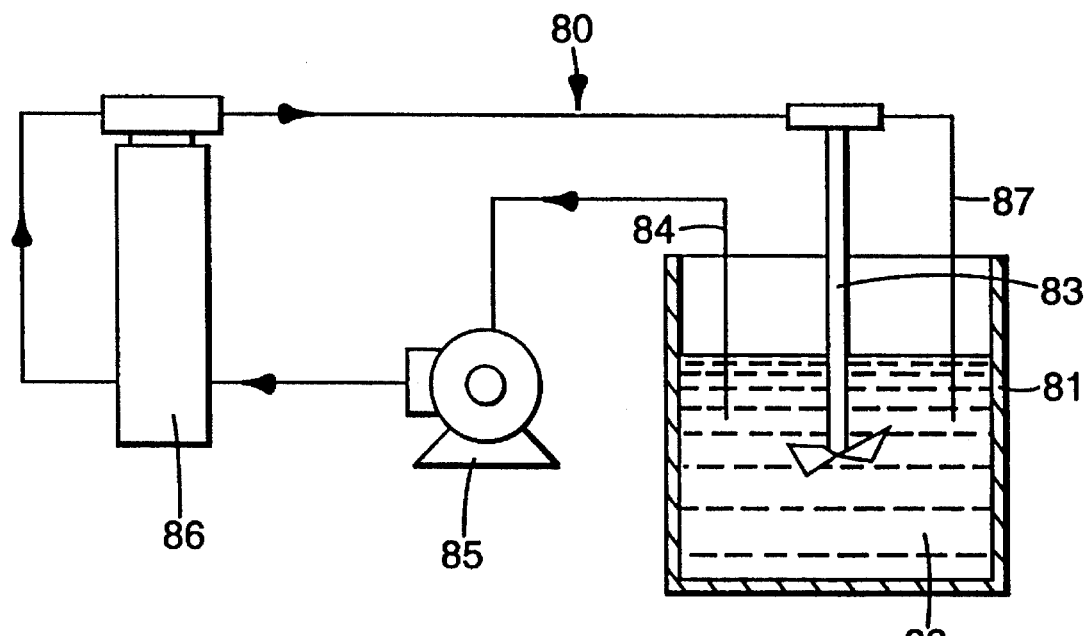
FIG. 6 is a schematic illustration of a separation system of the invention.

FIG. 6 is a schematic illustration of a separation system 80 of the invention. Reservoir 81 contains aqueous stationary phase particulate slurry 82 and/or biomacromolecule solution mixture 82, with stirring being provided by stirring apparatus 83. Slurry or solution 82 is pumped from outlet tube 84 by pump 85 through separation filter assembly 86 (which contains stationary phase particulates located on the upstream surface of the filtration layer of a filter cartridge (not shown)) and back into the reservoir via inlet tube 87 (arrows show direction of liquid flow).

Figure 7:
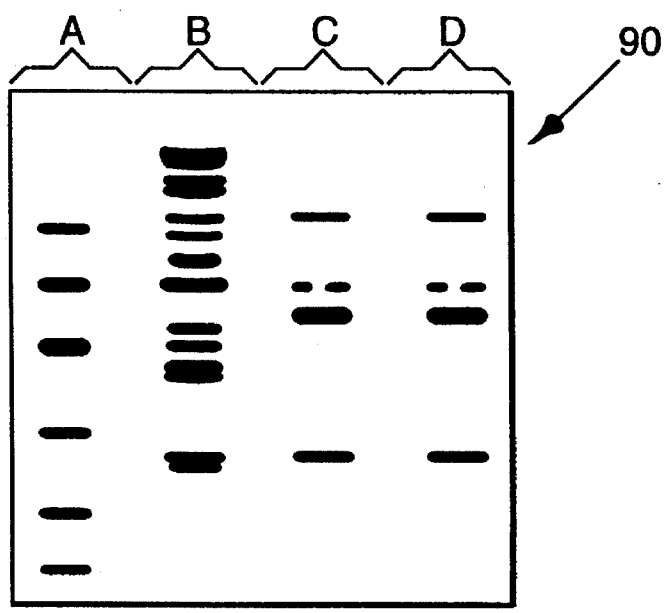
FIG. 7 depicts stained protein gel electrophoresis patterns of comparative proteins and a purified protein of the invention.

FIG. 7 shows a stained polyacrylamide electrophoretic gel 90. Lane A depicts the protein electrophoresis separation pattern achieved with a commercial mixture (available from Pharmacia LKB Biotechnology, Uppsala, Sweden) of known proteins (listed in order of increasing migration distance from the origin; approximate molecular weight in Daltons is also given): phosphorylase b (94,000), bovine serum albumin (67,000), ovalbumin (43,000), carbonic anhydrase (30,000), soybean trypsin inhibitor (20,100), and alpha-lactalbumin (14,400). Lane B depicts the large number of proteins comprising cryo-poor human blood plasma. Lane C depicts the protein electrophoresis pattern of commercial (Sigma Chemical Co., St. Louis, Mo.) human immunoglobulins, and lane D depicts the protein electrophoresis pattern of the protein eluate of Example 5.

DETAILED DESCRIPTION OF PREFERRED EMBODIMENTS

This invention provides a method of isolating and purifying a biomacromolecule comprising a separation filter assembly including a filter element which incorporates stationary phase particulates which can bind to a biomacromolecule on the upstream surface of a filtration layer. The separation filter assembly comprises a liquid filter cartridge which includes the above-described filter element and a suitable cartridge housing for the filter element connected to a reservoir of solution comprising one, or preferably two or more biomacromolecules. The filter cartridge is connected by suitable tubing to a pump capable of passing the solution, which can include a selected biomacromolecule to be separated by binding to particulate or an eluting solution to release the bound biomacromolecule, through the filter element and back into the reservoir so that the resultant solution can be repeatedly cycled through the filter element for further capture of the free biomacromolecule to complete the separation, or, if desired, to elute the bound biomacromolecule.

More particularly, the invention provides a method of separating or purifying a biomacromolecule, the method comprising the steps of:

1) providing a separation system containing a dead end filter cartridge comprising a composite filter medium, on the upstream surface of which are located stationary phase particulates capable of adsorption, ion exchange, hydrophobic, or affinity binding with a biomacromolecule, a reservoir containing a solution mixture comprising one or more than one biomacromolecule solute, a pump and associated tubing to form a closed loop system;

2) recirculation pumping the solution mixture through the filter cartridge assembly to accomplish binding of the selected biomacromolecule to the stationary phase particulates, the pumping through the filter element being conducted with a flux rate of at least 0.01 cm/minute, preferably at least 0.10 cm/minute, and more preferably at least 0.30 cm/minute at a filter cartridge pressure of at most 0.25 MPa;

3) optionally, washing the biomacromolecule: stationary phase particulate product with suitable liquid to remove unwanted biomacromolecules and other solutes not bound to the stationary phase particulates by the selected adsorption, ion exchange, hydrophobic or affinity binding interaction, in an open loop or one pass procedure; and 4) optionally pumping, preferably a decreased volume (compared to the original solution mixture volume), of a debinding solution containing a solute which will reverse the biomacromolecule:stationary phase particulate binding interaction to liberate the separated and purified biomacromolecule.

In the prior art, removal of particulates by filtration of liquid streams has been accomplished by applying one or a combination of the following filtration mechanisms, and liquid filter cartridges are presently commercially available that operate by each mechanism. The present invention utilizes a modification of these filter cartridges whereby the filtration layers retain stationary phase particulates in a flowing separation system.

i) Depth Filtration—This procedure is one in which a particulate-containing liquid stream is confronted by a filter element possessing a distribution of sized holes or pores and offers the particulates a rather tortuous pathway through the filtration layer. In the prior art, particulates were chiefly removed by adsorption and/or entrapment within the filtration layer itself. Depth filtration, often the coarse or first filtration procedure applied to a system and one designed to remove particulates having a size from hundreds of micrometers (in diameter-largest dimension) to about 1 micrometer, suffers problems of incomplete removal of particulates due to ill-defined pore sizes and steady, rapidly increasing filter cartridge pressures as the filter becomes loaded.

ii) Surface (Cake) Filtration—This procedure is preferred in the present invention and often occurs subsequent to depth filtration in the treatment of a liquid stream. In the prior art, it was generally conducted using multiple layers of glass or polymeric microfibers which possessed well-defined pore sizes, and the particulates generally did not penetrate within the filtration layer but remained trapped on the upstream surface of the layer. Particulate sizes down to about 1.0 micrometer were collected with efficiencies as high as 99.99%. High flux rates were readily achievable, and relatively large quantities of particulates were removed at relatively low system pressures until the filter was nearly full. In the present invention, it may be advantageous to remove or realign the filtered particles on the surface of the filtration layer by multiple reverses of the liquid flow; this opportunity does not exist with depth filters.

iii) Membrane (Screen or Sieving) Filtration—This filtering mechanism is very similar to surface filtration, except that precisely defined, very small pores are present that are capable of removing virtually all particulates with sizes as low as 0.05 microns. While providing "absolute" control of particulates remaining in the stream, problems of low flow rates, low capacity, high pressures, and clogging also attend this filtration mechanism.

Useful surface filter cartridges in the present invention include the standard vertical pleated filters of U.S. Pat. No. 3,058,594 and, especially preferred, the horizontal, compound radially pleated filters of U.S. Pat. No. 4,842,739, all incorporated herein by reference as useful particle loadable filter cartridges for the present invention. A horizontal arrangement of pleats (as shown in FIG. 3) is preferred in the present invention because the filter cartridges are generally employed vertically, and a greater percentage of particles is retained within the horizontal pleats when flow is discontinued and the cartridge stored between uses. Other filter cartridges such as string wound, resin bonded, and spray spun depth filters may also be utilized but generally lack the ability to accept as much particulate as the surface filters while at the same time maintaining relatively low system pressures.

Standard cylindrical, vertically pleated filter cartridges are available from Ameteck Inc. (Sheboygan, Wis.) in a variety of sizes, e.g., 4.8×24.8 cm (diameter×height), 6.7×24.8 cm, 6.7×50.8 cm, 11.4×24.8 cm, and 11.4×50.8 cm, with filter element materials, e.g., cellulose, cellulose-polyester, glass-cellulose, polyester, polypropylene, and ceramic, and having average nominal pore sizes, e.g., 1, 2, 3, 5, 10, 20, 30, and 50 micrometers. Preferred cylindrical, compound horizontally radially pleated surface filter cartridges of all-polypropylene construction can be purchased from 3M Filtration Products (St. Paul, Minn.) in a variety of sizes, e.g., 6.4×25.0 cm, 6.4×50.0 cm, 6.4×75.0 cm, and 18.0×100.0 cm, and possessing average nominal pore sizes of 2, 5, 10, and 20 micrometers. Smaller disposable capsule filters that are useful for smaller scale separations are available from Gelman Sciences, Inc. (Ann Arbor, Mich.) in a variety of sizes, e.g., 6.3×6.4 cm, 5.8×17 cm, and 8.6×14 cm, with filter element materials, e.g., polyamide such as acrylic coated Nylon and polypropylene, and average nominal pore sizes, e.g., 1, 3, and 5 micrometers.

While the binding (separation step) and elution (isolation step) interactions can be conducted using filter cartridge housings available from filter cartridge manufacturers, these housings generally possess only one set of inlet and outlet ports. As a consequence, it is difficult to accomplish the highly desirable concentration of the purified biomacromolecule when the debinding solution is introduced. A preferred filter cartridge housing of all-polypropylene construction, available from Ultra Filter Systems (Brooklyn Center, Minn.), possesses an additional set of inlet and outlet ports of smaller size. This smaller set of ports can advantageously be utilized to accomplish debinding of the biomacromolecule, generally in a significantly reduced total volume of solution so that the purified biomacromolecule is obtained in a more concentrated solution in the process as well.

Preferably, the composition of the filtration medium of the present invention comprises one or more nonwoven layers on the upstream surface of which are randomly disposed insoluble stationary phase particulates. From a mechanical standpoint and with regard to solvents employed, compositions of filtration media are not critical when conducting separations because water is utilized almost exclusively, and essentially all of the above-specified filtration layer materials generally perform well in water. A preferred material because of its availability, cost, and inertness is polypropylene.

Selection of the pore size of the filtration layer depends directly on the size range of the stationary phase particulates to be retained on the upstream surface thereof and generally corresponds with the smallest particulate size. It has been determined, however, that even if a portion of the particulates possesses sizes smaller than the pore size of the filtration layer useful composite filtration media can be obtained. Because of the method of preparing the partially loaded filtration media vide infra these smaller particulates will pass through the filtering element in early cycles, in later cycles as a bed of particulates accumulates the device takes on the nature of a depth filter, and these smaller particles can also be removed and utilized in the invention. In the interests of time efficiency and utilizing the filter cartridge in the preferred surface filtration mode, however, it is preferable to utilize a surface filter cartridge unit wherein at least 95% of the stationary phase particulates are removed in the first pass through the filter. Generally a filter cartridge rated nominally at an average of 1–10 micrometers meets these criteria and provides an efficient filtering element for the particulates utilized in the invention and also is capable of delivering relatively high flux rates at low filter cartridge pressures. Filtration layers with average pore sizes less than 1.0 micrometer such as porous, nonfibrous membranes are not generally useful because they are susceptible to plugging, not only from adventitious particles that may be present but even by suspended biological material which is often encountered in highly concentrated biological solution mixtures.

For purposes of this invention, stationary phase particulates bind or strongly associate with the biomacromolecules of interest in solution mixtures by one or a combination of the following interactions: adsorption, ion exchange, hydrophobic association, and affinity binding. The sizes of the stationary phase particulates useful in the invention can range from a distribution in which a small portion, e.g., less than 5%, are submicrometer (largest diameter) to as large as several millimeters depending on the nature of the filter cartridge employed. Discussion and caveats relating to the lower size limit of particulates have already been given in relation to selection of a proper pore size filtering layer. The upper size limit of the particulates will depend on the particular kind of filter cartridge and is ultimately determined by the separation of pleat or fold tips. Particulate sizes are required to be less than the distance between pleat or fold inlet tips so that penetration within and on the upstream surface of the pleats or folds of the filtering element can occur. As a matter of working practicality, experience has shown that in order to prevent aggregates of particles from exceeding the pleat/fold tip distance, a significantly smaller particle size, i.e., approximately ⅕ or less of the pleat/fold tip distance, preferably is utilized. An important attribute of the present invention is that a greater quantity of the selected biomacromolecule can generally be separated by utilizing a particulate support possessing a relatively high surface area. Preferably, the surface area is at least 10 $m^2/g$, more preferably at least 50 $m^2/g$, and most preferably at least 100 $m^2/g$, and even up to 5000 $m^2/g$ (as determined by gas adsorption measurements). Particle sizes of stationary phase materials are preferably in the range of submicrometer to 400 micrometers, more preferably 1–200 micrometers, and most preferably 10–100 micrometers in diameter.

Various interactions between solutes and stationary phase particulates can involve relatively weak attractive forces such as dipole-dipole, ion-dipole, and ion-ion interactions. What makes biomacromolecules having a molecular weight of at least 500 efficiently bound in the present invention is that several of these interactions occur over the relatively large area of contact between biomacromolecule and stationary phase, resulting in a net strong attractive force.

Adsorption chromatography utilizes the binding association of polar groups on a stationary phase and the wide diversity of polar groups on biomacromolecules. These binding associations are generally of the form of dipole-dipole and ion-dipole interactions. The binding or separation phase of the purification operation is usually conducted from an aqueous buffered solvent of relatively low ionic strength so that the above-mentioned binding associations between stationary phase and biomacromolecule solute can be maximized to effect binding. After washing with a buffered aqueous solution of low ionic strength, the eluting solution commonly employed contains a relatively large amount of dissolved salts and a concomitant high ionic strength so that interactions between the stationary phase and the dissolved salts will displace the biomacromolecule from the stationary phase, and the biomacromolecule will re-dissolve and can be recovered in purer form from the separation system.

Preferred adsorption stationary phase particulates include hydroxylapatite (available from BioRad Laboratories, Richmond, Calf.), alumina (available from EM Separations, Gibbstown, N.J.), silica gel (also available from EM Separations), and zirconia (disclosed in U.S. Pat. No. 5,015,373 and incorporated by reference).

Ion exchange chromatography takes advantage of the fact that many biomacromolecules are ionically charged. Furthermore, many of these ionically charged groups, e.g., protonated amine and carboxylate, can be rendered neutral and uncharged by a change in pH. This provides a sensitive and very powerful technique for separation of biomacromolecules based on their isoelectric points, often indicated by a pI value which is the pH at which charge neutrality exists or the number of negatively charged groups and positively charged groups within a structure is the same. If the pH is maintained above pI, then an anion exchange resin can be used to bind the biomacromolecule; conversely, if the pH is lower than pI, a cation exchange resin can effect binding and removal of the biomacromolecule from the solution mixture. With this technique even small differences in accessible or surface charges on biomacromolecules can result in effective separations. After washing the insolubilized biomacromolecule:stationary phase particulate product, elution of the bound biomacromolecule from an ion exchanging stationary phase particulate is generally conducted by introducing a relatively high concentration of a salt solution whose corresponding ions will exchange with and displace the biomacromolecule from the stationary phase particulate.

Useful ion exchange stationary phase particulates are available from several vendors including Pharmacia LKB Biotechnology, Inc. (Piscataway, N.J.), Toso Haas (Philadelphia, Pa.), EM Separations (Gibbstown, N.J.), and Biosepra, Inc. (Marlborough, Mass.). Useful anion exchanging resins feature agarose, dextran, and cellulose polymers that have been modified to contain diethylaminoethyl and quaternary ammonium groups. Cation exchanging resins feature the same base polymers but possessing carboxylate and sulfonate groups.

Hydrophobic interaction chromatography utilizes the principle of "like dissolves like" and the hydrophobicity of many biomacromolecules. Intercalation of hydrophobic portions of a biomacromolecule into hydrophobic pockets of a stationary phase particulate results in a binding association and separation of the biomacromolecule from the solution mixture. The procedure is commonly conducted by binding from an aqueous solution of relatively high ionic strength. In this fashion the biomacromolecule is somewhat precariously soluble to begin with by being almost "salted out" of solution and will readily bind to a hydrophobic solid support. Elution is commonly conducted by employing an aqueous solution of reduced ionic strength (and increased solvent efficiency for the biomacromolecule); alternatively, organic solvents such as acetone, acetonitrile, ethanol, methanol, and N,N-dimethylformamide in amounts up to 50 weight percent may be employed with water as co-solvent to remove the biomacromolecule from the insoluble complex with the stationary phase particulate.

Useful hydrophobic interaction stationary phase particulates can be purchased from Pharmacia, among other vendors, and feature agarose base supports. Any of the hydrophobic interaction stationary phase particulates can be modified by inclusion of butyl, octyl, and phenyl groups.

Affinity chromatography operates generally by covalently binding a ligand or biospecific effector to a stationary phase particulate. This ligand or effector is chosen because of its ability to interact with a biomacromolecule by a "lock and key" relationship. If a protein, for example, is the biomacromolecule whose separation is desired, the covalently bound ligand or effector is often a substrate or inhibitor ("key" molecule) which binds strongly to the active site (the "lock") of the protein. The high selectivity of this process allows for one step purification of a biomacromolecule from a complex mixture. Although elution is often accomplished by a simple change in pH, debinding solutions and techniques are specific for each biomacromolecule-ligand pair, and specific instructions can be obtained from the manufacturer.

Useful affinity chromatography stationary phase particulates are available from Pharmacia, Toso Haas, EM Separations, Biosepra, Inc., and 3M Bioapplications (St. Paul, Minn.). A variety of base particulate supports including agarose, cellulose, and vinyl polymers is available, for example, from Pharmacia, Piscataway, N.J., possessing several ligands (with corresponding biomacromolecule affinities) including: arginine and benzamidine (serine proteases), Cibacron Blue (enzymes requiring adenyl-containing cofactors, albumin, coagulation factors, interferon), calmodulin (ATPases, protein kinases, phosphodiesterases, neurotransmitters), gelatin (fibronectins), glutathione (Stransferases, glutathione-dependent proteins, fusion proteins), heparin (growth factors, coagulation proteins, steroid receptors, restriction endonucleases, lipoproteins, lipases), Proteins A and G (IgG and subclasses), L-lysine (plasminogen, plasminogen activator, ribosomal RNA), procion red ($NADP^+$ dependent enzymes, carboxypeptidase G), concanavalin A and lectins (glycoproteins, membrane proteins, glycolipids, polysaccharides), and DNA (DNA polymerase, RNA polymerase, T-4 polynucleotide kinase, exonucleases).

Having thus described the filter cartridges, filter housings, and stationary phase particulates, the process by which the separation systems are prepared will now be detailed. The process involves the steps of:

i) providing a closed loop assembly comprising a filter cartridge comprising a composite filter medium of the invention contained in a housing, a reservoir containing a slurry of the insoluble stationary phase particulates in a liquid, and a pump and associated tubing capable of delivering a flux rate of at least 0.01 cm/minute;

ii) pumping the slurry through the filter cartridge in a recycling mode until the desired amount of stationary phase particulates has been loaded; preferably the filter cartridge pressure is less than about 0.15 MPa, more preferably less than 0.10 MPa, and most preferably less than 0.05 MPa; and iii) introducing a biological solution mixture which comprises at least one biomacromolecular solute into the reservoir so that it can undergo circulation in the separation filter assembly to effect separation of the biomacromolecule.

Pumps useful in the invention provide flux rates through the filter cartridge in excess of 0.01 cm/minute, preferably in excess of 0.10 cm/minute, and more preferably in excess of 0.30 cm/minute. The pumps and associated gasketing and tubing/piping through which at least one of the slurry and solution mixture comprising more than one biomacromolecule solute flow preferably are relatively chemically unaffected by the solution. Preferred pumps include peristaltic, diaphragm, gear, and centrifugally driven pumps in which the actual pump components contacting the solution are constructed of stainless steel or polytetrafluoroethylene (PTFE). Most types of rubber or plastic tubing/piping are suitable for packings and separations conducted in aqueous media, but if aqueous mixtures of organic solvents are employed, polypropylene, polyethylene, PTFE, stainless steel, and glass tubing preferably are employed. Preferred gasketing materials to interface the connection of the filter cartridges to filter housings and with the rest of the separation system include PTFE and polypropylene.

In contrast to conventional "dry" packing manufacturing techniques, "wet" packing the particulates onto the filtration layer by use of a liquid carrier assures that the particulates are located in regions of the filtering element which are subsequently accessible to solution mixtures. The particulates are randomly located on the filtration layer in the sense that their positions are not preselected, although the flow of the liquid carrier may influence the ultimate location of particulates. In packing the filter cartridge by the above process it is desirable to employ fairly dilute concentrations of the particulates in the liquid during each packing session in order to achieve relatively uniform partial loading of the filtering element. The particulates can be added to the reservoir in a portionwise fashion (either without solvent if suitably dense and water-wettable or pre-slurried), with visual clarification of the reservoir contents occurring between each portion. The flux rate of the packing operation preferably is at least 0.01 cm/minute, more preferably at least 0.10 cm/minute, and most preferably at least 0.30 cm/minute. In addition to separating desired biomacromolecules efficiently with regard to quantity and time during the separation phase, relatively high flux rates are desirable during the particle loading phase especially with the preferred compound radially pleated filter cartridges so that the particulates can better permeate the folds of the pleated filter element, thus accessing more of the filter element and facilitating high loading. The liquid employed to slurry the stationary phase particulates generally is the solvent of the solution mixture and is generally water, preferably buffered water. With hydrophobic interaction stationary phase particulates it may be necessary, especially in the elution step, to utilize organic liquids, in combination with water. Useful organic liquids include methanol, ethanol, isopropanol, acetonitrile, and N,N-dimethylformamide in amounts up to 50 weight percent.

The particulates are loaded into the reservoir and ultimately onto the upstream surface of the filter element until the filter cartridge pressure reaches not more than 0.15 MPa, preferably not more than 0.10 MPa, and more preferably not more than 0.05 MPa. A practical filter cartridge pressure limit for a fully loaded preferred compound radially pleated filter cartridge is about 0.25 MPa. As a general rule of application of filter cartridges, when filter cartridge pressures in excess of about 0.05 MPa are attained, subsequent loading of additional particulates results in increasingly higher filter cartridge pressures. Especially with the lower recommended filter cartridge pressures, however, flux rates of solutions passing through the filter cartridges remain high and in the range desirable for the purposes of this invention. In this fashion, the unit can still respond to adventitious particulates that are likely to be encountered during subsequent separation and handling operations. By reserving some particulate loading capacity for actual operation, shut downs due to filter plugging are averted and filter cartridge lifetimes can be extended.

The stationary phase particulate loaded filter cartridge is now ready to be utilized as a separation filter assembly to separate a biomacromolecule from a solution mixture passed through. The separation filter assembly and cartridge are schematically illustrated in FIGS. 1–5.

After loading the particulates to provide the composite filtration media, the inlet and outlet tubing ends are removed from the reservoir (or left attached if the packing reservoir will also function as separation reservoir) and are attached to a reservoir containing a biological solution mixture. Biological solution mixtures can comprise more than one biomacromolecule solute which is (or at one time was) a component or product of a cell. The desired biomacromolecule can be a product that is excreted from a cell or an intracellular component obtained after lysis of the cell's outer membrane or wall. Useful biological solution mixtures include fermentation media, cell lysates, and body fluids such as blood and blood components, ascitic fluids, and urine.

It is normally desired to obtain the greatest quantity of purified biomacromolecule in the shortest period of time. The velocity with which a solution mixture is passed through the composite filtration medium, i.e., the flux rate, and recycled has been determined to be an important criterion for performance in the present invention. One very important factor is that the present invention separation filter assemblies permit larger volumes of solution mixtures to be processed in a given time primarily because of low pressure operation. Other factors which may contribute to the high efficiencies of the present invention separation filter assemblies are: 1) the ability to utilize smaller stationary phase particulates possessing relatively high surface areas and reduced diffusional limitations compared to larger particles utilized in packed columns; 2) better shear mixing of the biomacromolecule solutes and the stationary phase particulates at higher flux rates; and 3) access to a greater number of particulates contained deeply within pleats or folds of the filtering element at higher flux rates. A flux rate of solution mixture passage of at least 0.01 cm/minute is preferred, more preferably at least 0.10 cm/minute, and most preferably at least 0.30 cm/minute.

The filter elements of the present invention find utility in a variety of biological separations involving proteins, carbohydrates, lipids, nucleic acids, and other biological materials. Separated and purified macromolecules are useful therapeutic and diagnostic agents.

Objects and advantages of this invention are further illustrated by the following examples, but the particular materials and amounts thereof recited in these examples, as well as other conditions and details, should not be construed to unduly limit this invention.

EXAMPLE 1

This example teaches use of a separation filter assembly of the invention in separating a biomacromolecule from a solution mixture using an adsorption interaction.

A separation system shown in FIG. 6 was constructed using a 6 liter beaker as packing and separation reservoir; a separation filter assembly consisting of a 2 μm nominal pore size, horizontal, compound radially pleated filter cartridge of all-polypropylene construction and possessing a filtration layer with a frontal surface area of 0.84 m² (Model 313 B, available from 3M Filtration Products, St. Paul, Minn.) and a Lexan filter housing (Model PSCL, available from Ametek, Sheboygan, Wis.); a Masterflex peristaltic pump (Model 7549-30, available from Cole-Parmer Instrument Co., Chicago, Ill.); and Masterflex Pharmed Norprene tubing (Model No. 6485-73, also available from Cole-Parmer).

A buffer solution (4 L of 0.005 M sodium dihydrogen phosphate and 0.005 M disodium hydrogen phosphate at pH 6.5) was placed in the reservoir, and hydroxylapatite (Biogel HTP™, available from Bio Rad Laboratories, Richmond, Calif.) (60 grams in 5 gram increments) was loaded onto the upstream surface of the filter cartridge using a flow rate of 3800 mL/minute (flux rate=0.45 cm/minute). A pressure gauge located on the upstream side of the separation filter assembly recorded an increase in pressure of only 0.02 MPa during the loading operation.

Separation Phase:

To the buffer solution in the reservoir were added 3.25 grams of hemoglobin (bovine, available from Sigma Chemical Company, St. Louis, Mo.) pre-dissolved in 500 mL of buffer, and the pump was started at a rate of 3800 mL/minute. Within 5 minutes, UV analysis (absorbance at 408 nm) showed that 95% of the hemoglobin had been removed from the reservoir solution.

Isolation Phase:

The contents of the reservoir were discarded, and the separation filter assembly was washed (in one pass) with 4 L of distilled water. Next, an eluting solution (0.25 M sodium dihydrogen phosphate and 0.25 M disodium hydrogen phosphate at pH 6.5) (3300 mL) was placed in the reservoir. Pumping was begun at 3800 mL/minute and 81% of the bound hemoglobin was recovered in 3300 mL of solution in 3 minutes based on UV absorptions.

EXAMPLE 2

This example shows the principle of the use and advantages of a separation filter assembly having different separation and isolation loops for purposes of increasing the concentration of a biomacromolecule.

A separation filter assembly shown in FIG. 5 was utilized and was obtained from Ultrafilter Systems (Brooklyn Center, Minn.). The unit featured all-polypropylene construction and a 3M (Model 313 B) filter cartridge; the separation loop fittings were 1.50 cm in diameter (inside), while the isolation loop fittings were 0.50 cm in diameter. Hydroxylapatite (60 grams) was loaded onto the filter cartridge as described in Example 1 using the same buffer solution, quantities, and flux rate.

Separation Phase:

Using the 1.50 cm fittings and a general arrangement depicted in FIG. 6 with 0.90 cm (inside diameter) tubing, hemoglobin (2.00 grams) was bound to the hydroxylapatite from a total system volume of 6100 mL using a flux rate of 0.45 cm/minute. After 30 minutes, UV analysis revealed that 95.8% of the hemoglobin had been removed from the reservoir solution. The unit was then washed (in one pass) with distilled water (4L).

Isolation and Concentration Phases:

The distilled water remaining in the separation filter assembly was drained through the center outlet port (0.50 cm fitting). Then, using the smaller set of fittings as the isolation loop and a smaller Masterflex pump (Model 7021-36) equipped with 0.50 cm (inside diameter) tubing, an eluting solution as disclosed in Example 1 (650 mL) was recirculation pumped at 500 mL/minute through the cartridge for 3 minutes; UV analysis of the solution when subsequently pumped and drained from the assembly showed 51% recovery of hemoglobin. Another 650 mL of debinding solution similarly employed removed an additional 19%. Therefore, 70% of the hemoglobin had been isolated and collected in more concentrated form in 1300 mL of solution, compared with the original volume of 6100 mL.

EXAMPLE 3

This example teaches use of an ion exchange stationary phase particulate for separating a biomacromolecule from a solution mixture containing more than one biomacromolecule. At pH 8.0, cytochrome C (pI=9.6) (horse heart, available from Sigma) was positively charged and was not bound by the positively charged, protonated diethylaminoethyl (DEAE)-functional stationary phase particulates. Bovine serum albumin (BSA; pI=5.5) (available from Miles Diagnostics, Kankakee, Ill.), on the other hand, was negatively charged and was bound at pH 8.0.

The separation system of FIG. 6 was utilized in which the separation filter assembly consisted of a filter cartridge (Model 313 B, 3M Filtration Products) and a filter cartridge housing depicted in FIG. 5 (Ultra Filter Systems). The reservoir contained 4 L of sodium citrate buffer solution (pH 6.0), and DEAE Sepharose Fast Flow™ (110–160 µeq./mL, available from Sigma) (500 mL) was portionwise loaded over the course of 30 minutes while pumping at 3800 mL/minute (flux rate=0.45 cm/minute). A corresponding filter cartridge pressure of about 0.01 MPa was observed over the packing period. A solution (25 mM; 3L) of EPPS (N-[ 2-hydroxyethyl]piperazine-N'-[3-propanesulfonic acid]) buffer (pH 8.0) (Sigma Chemical Co., St. Louis, Mo.) was then pumped (one pass) through the separation filter assembly to replace the packing citrate buffer.

Separation Phase:

The solution in the reservoir was replaced with 3850 mL of 25 mM EPPS buffer (pH 8.0). A solution mixture consisting of 100 mg of cytochrome C (horse heart, available from Sigma), 500 mg of BSA and 40 mL of EPPS buffer was added to the reservoir bringing the total separation system volume to 5350 mL (3850 mL+40 mL+1460 mL (volume in separation filter assembly and tubing)). The UV spectrum of the solution in the reservoir was recorded, with special attention being paid to the absorbance at 280 nm which was 0.199 (chiefly due to BSA); cytochrome C exhibited a major peak at 408 nm (A=0.231). The pump was engaged at 3000 mL/minute (flux rate=0.36 cm/minute), and aliquots were removed from the reservoir every two minutes. Approximately 20 minutes of recirculation pumping were required until the absorbance at 280 nm diminished no further; the absorbance at 408 nm remained essentially unchanged in all of the aliquots. Thus, cytochrome C remained in solution while the BSA became ionically bound onto the stationary phase particulates in the separation filter assembly.

Isolation Phase:

First the separation filter assembly was washed (one pass) with 3 L of 25 mM EPPS. Then, using the same loop, i.e., the 1.5 cm fittings, 1 M NaCl was pumped (flux rate=0.36 cm/minute) through the unit (one pass). UV analysis of the eluant revealed that 67% of the purified BSA was obtained in the first 3 L.

EXAMPLE 4

This example teaches the separation of BSA and cytochrome C using hydrophobic interaction binding.

Macro Prep™ t-Butyl HIC™ Support (available from Bio-Rad Laboratories, Hercules, Calif.) which features a hydrocarbon polymer backbone and pendent t-butyl groups was utilized as the hydrophobic interaction stationary phase particulate. The support consisted of beads possessing a nominal bead diameter of 50 micrometers; the material was available as a slurry in 20 weight percent ethanol-water, and the dry polymer content was 18.6% by weight. This material (40 mL of the slurry; 7.68 grams) was added in 5 mL portions to a reservoir containing 2M ammonium sulfate. The particulates were loaded by the procedure of Example 1 onto the upstream surface of a polypropylene filter cartridge (3M; Model 313B) employed in a configuration as depicted by the separation system shown in FIG. 6 using a flow rate of 4926 mL/minute (flux rate=0.59 cm/minute); total system volume was 6004 mL and the pH was 5.4.

Preliminary UV analyses were conducted on cytochrome C and in combination with an equal weight of BSA. Ratios of absorbances at 280 nm/408 nm for cytochrome C were 0.148/0.453=0.327 and in combination with BSA an absorbance ratio of 0.179/0.461 =0.388.

The separation system was then challenged with 300 mg of cytochrome C and 300 mg of BSA by adding the protein solids to the reservoir and stirring. When dissolved, the pump was begun at the above flux rate, and 1 mL aliquots were withdrawn at various times and the optical densities at 280 and 408 nm were measured. The data is shown in Table 1, below.

TABLE 1

| Time (minutes) | Optical Density (OD) at 280 nm | OD at 408 nm | 280/408 Ratio |
| --- | --- | --- | --- |
| 5 | 0.174 | 0.466 | 0.373 |
| 10 | 0.174 | 0.460 | 0.366 |
| 15 | 0.167 | 0.460 | 0.363 |
| 30 | 0.163 | 0.456 | 0.357 |
| 45 | 0.161 | 0.452 | 0.356 |
| 60 | 0.164 | 0.455 | 0.360 |

The data of Table 1 show that the more polar cytochrome C remained in solution while the relatively hydrophobic BSA (near its pI of 5.6) was bound selectively onto the stationary phase particulates of the separation filter assembly.

At this point the assembly can be washed with 2M ammonium sulfate in a one-pass operation to remove all nonspecifically bound biomacromolecules. The BSA can then be isolated by passing an eluting solution consisting of a reduced ionic strength solution such as 0.1 M ammonium sulfate, preferably at the same pH, through the unit.

EXAMPLE 5

This example teaches the use of a separation filter assembly of the invention to separate specific biomacromolecules from a solution mixture comprising many biomacromolecules using an affinity interaction.

A modified version of the separation system of FIG. 6 was utilized in which the filter cartridge comprised a 2 µm nominal porosity horizontal, compound radially pleated filter possessing a surface area of 0.37 m² (available from 3M Filtration Products, St. Paul, Minn.). Also, an in-line UV absorbance monitor (Model UA-5; available from ISCO Instrument Co., Lincoln, Nebr.) was incorporated on the downstream side of the separation filter assembly. A buffer solution (4 L) consisting of 0.15 M sodium chloride, 0.003 M sodium dihydrogen phosphate, and 0.017 M disodium hydrogen phosphate (pH=7.4) was added to the reservoir and recirculated through the system using a flow rate of 4000 mL/min. (flux rate=1.08 cm/min). The filter assembly was carefully vented to remove all trapped air. EMPHAZE™ Biosupport Media derivatized with recombinant Protein A (80 mL; available from 3M Bioapplications, St. Paul, Minn.) was added to the packing reservoir in 20 mL aliquots and was loaded onto the upstream surface of the filter element using recirculation pumping at 4000 mL/min. After all the Protein A-functional stationary phase particulates had been deposited, the system flow rate was increased to 6000 mL/minute for 2 min. to ensure that the particles were deposited into the pleat folds. System flow rate was then reduced to 1000 mL/min. and the assembly was washed in one pass with 6 L of buffer solution. At this point, system flow was stopped, and the packing reservoir was replaced by a 4 L polypropylene container equipped with a magnetic stirring bar in order to perform the separation operation.

Separation Phase:

The separation reservoir was charged with 2000 mL of buffer solution described immediately above and the system flow rate was 1000 mL/min. (flux rate=0.27 cm/min.). Filtered cryo-poor human blood plasma (350 mL; obtained from the American Red Cross St. Paul Regional Blood Center, St. Paul, Minn.) was added to the reservoir, and recirculation was continued for 30 min. The system was then washed with 4 L of fresh buffer solution in one pass.

Isolation Phase:

Protein captured in the separation filter assembly was then eluted using a solution (2 L) consisting of 0.1M glycine and 2 volume % acetic acid (pH=2.2). This solution was recirculation pumped through the assembly for 15 min. at 1000 mL/min. Eluted protein was then isolated by one pass pumping the system and adding fresh buffer to the reservoir until a total of 4000 mL was collected.

The eluant was then analyzed to determine the identity, purity, and concentration of separated proteins. Analysis of chemically reduced samples of the eluate with SDS gel electrophoresis (Pharmacia PhastGel™, 8–25% gradient gel with silver stain) (FIG. 7) indicated that the eluted protein was composed almost entirely of immunoglobulins by comparison with an authentic commercial sample. Measurement of the optical density of the recovered eluate at 280 nm indicated that the concentration of protein was approximately 0.27 grams/liter. Therefore, approximately 1.08 grams of pure human immunoglobulins were recovered from the 350 mL of blood plasma. This corresponds to a yield of about 31% if the immunoglobulin concentration in cryo-poor human plasma is assumed to be 10 grams/liter.

Various modifications and alterations of this invention will become apparent to those skilled in the art without departing from the scope and spirit of this invention, and it should be understood that this invention is not to be unduly limited to the illustrative embodiments set forth herein.

We claim:

1. A method of separating a biomacromolecule from a solution mixture comprising the steps of
    a) providing a separation system containing a dead end filter cartridge comprising a composite filter medium including a porous filtration layer on the upstream surface of which is located a layer of stationary phase particulates capable of binding with a biomacromolecule, a reservoir containing a solution mixture comprising at least one biomacromolecule as a solute, and a pump and associated tubing to form a closed loop assembly, and
    b) recirculation pumping the solution mixture through the filter cartridge at a flow rate of at least 37 mL/min. so as to bind said at least one biomacromolecule to the stationary phase particulates so as to form a biomacromolecule:stationary phase particulates product.

2. The method according to claim 1 further comprising the step of:
    pumping an eluting solution through the closed loop assembly which is capable of reversing the biomacromolecule:stationary phase particulates product binding interaction so as to liberate the biomacromolecule.

3. The method according to claim 1 further comprising the step of washing the biomacromolecule: stationary phase particulate product with liquid to remove unwanted biomacromolecules and solutes not bound to the stationary phase particulates.

4. The method according to claim 1 wherein said stationary phase particulates are selected from the group of particulates capable of binding by adsorption, ion exchange, hydrophobic binding, and affinity binding.

5. The method according to claim 1 wherein said pumping of said solution mixture through the filter cartridge is at a flux rate of at least 0.01 cm/minute, at a filter cartridge pressure of at most 0.25 mPa.

6. The method according to claim 5 wherein said flux rate is at least 0.10 cm/minute.

7. The method according to claim 5 wherein said filter cartridge pressure is at most 0.15 MPa.

8. The method according to claim 1 wherein said biomacromolecule is selected from the group consisting of a protein, carbohydrate, lipid, and nucleic acid.

9. The method according to claim 1 wherein said composite filter medium comprises a woven or nonwoven porous material.

10. The method according to claim 9 wherein said filter medium material is selected from the group consisting of cellulose, glass, polyolefin, polyester, polyamide, and ceramic.

11. The method according to claim 10 wherein said filter medium material has an average nominal pore size in the range of 1 to 50 micrometers.

12. The method according to claim 9 wherein said filter medium material is polypropylene.

13. The method according to claim 1 wherein said stationary phase particulates have a surface area of at least $10 m^2/g$.

14. The method according to claim 1 wherein said stationary phase particulates have a particle size in the range of submicrometer to 400 micrometers.

15. The method according to claim 1 wherein said particulates are adsorption stationary phase particulates.

16. The method according to claim 15 wherein said adsorption stationary phase particulates are selected from the group selected from hydroxylapatite, alumina, silica gel, and zirconia.

17. The method according to claim 1 wherein said stationary phase particulates are ion exchange particulates.

18. The method according to claim 17 wherein said ion exchange particulates are selected from the group consisting of anion exchanging resins and cation exchanging resins.

19. The method according to claim 1 wherein said stationary phase particulates are hydrophobic interaction stationary phase particulates.

20. The method according to claim 19 wherein said hydrophobic interaction stationary phase particulates are supports comprising at least one of butyl, octyl, and phenyl groups.

21. The method according to claim 1 wherein said particulates are affinity chromatography stationary phase particulates.

22. The method according to claim 21 wherein said affinity chromatography stationary phase particulates are selected from the group consisting of agarose, cellulose, and vinyl polymers comprising ligands with biomacromolecule affinity.

23. The method according to claim 1 wherein said solution mixture comprises a mixture selected from the group consisting of fermentation media, cell lysates, and body fluids.

24. The method according to claim 23 wherein said body fluid is selected from the group consisting of blood, an ascitic fluid, and urine.

25. The method according to claim 24 wherein said body fluid comprises at least one blood component.

26. The method according to claim 1 wherein said solution mixture comprises two or more biomacromolecules.

27. The method according to claim 1 wherein the recirculation pumping causes the concentration of the separated biomacromolecule to be increased relative to the concentration of the biomacromolecule in the solution mixture.

28. The method according to claim 1 wherein the flow rate of the solution mixture through the filter cartridge is at least 370 mL/min.

29. An apparatus for separating a biomacromolecule comprising a) a separation system containing a dead end filter cartridge comprising a composite filter medium including a porous filtration layer on the upstream surface of which is located a layer of stationary phase particulates capable of binding with a biomacromolecule, a reservoir containing a solution mixture comprising at least one biomacromolecule as a solute, and a pump and associated tubing to form a closed loop assembly, and the closed loop assembly providing for recirculation pumping of the solution mixture through the filter cartridge at a flow rate of at least 37 mL/min. so as to bind said at least one biomacromolecule to the stationary phase particulates so as to form a biomacromolecule:stationary phase particulates product.

30. The apparatus according to claim 29 further comprising means for pumping an eluting solution through the closed loop assembly which is capable of reversing the biomacromolecule:stationary phase particulate product binding interaction so as to liberate the biomacromolecule.

\* \* \* \* \*

UNITED STATES PATENT AND TRADEMARK OFFICE
CERTIFICATE OF CORRECTION

PATENT NO. : 5,468,847
DATED : November 21, 1995
INVENTOR(S) : Steven M. Heilmann et al.

It is certified that error appears in the above-indentified patent and that said Letters Patent is hereby corrected as shown below:

Col. 11, line 29, "(Stransferases," should be -- (S-transferases, --.

Col. 19, line 13, delete "an".

Signed and Sealed this

Sixth Day of August, 1996

*Attest:*

BRUCE LEHMAN

*Attesting Officer*    *Commissioner of Patents and Trademarks*